United States Patent
Kronenthal et al.

(10) Patent No.: US 6,340,752 B1
(45) Date of Patent: Jan. 22, 2002

(54) DEPROTECTION AND RECRYSTALLIZATION PROCESSES

(75) Inventors: David R. Kronenthal, Yardley, PA (US); Theodor Denzel, Regensburg (DE); Bang-Chi Chen, Plainsboro, NJ (US); James H. Simpson, Belle Mead, NJ (US); Rajendra P. Deshpande, Neshanic Station, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/208,135

(22) Filed: Dec. 9, 1998

Related U.S. Application Data

(60) Provisional application No. 60/070,573, filed on Jan. 6, 1998.

(51) Int. Cl.$^7$ .................. C07D 281/02; C07D 513/02
(52) U.S. Cl. .................. 540/490; 540/521; 540/523; 544/47; 544/48; 544/90; 544/91
(58) Field of Search .................. 540/490, 521, 540/523; 544/47, 48, 90, 91

(56) References Cited

U.S. PATENT DOCUMENTS

| | | | | |
|---|---|---|---|---|
| 5,362,727 A | | 11/1994 | Robl | 514/214 |
| 5,504,080 A | | 4/1996 | Karanewsky | 514/214 |
| 5,508,272 A | * | 4/1996 | Robl | 514/80 |
| 5,525,723 A | | 6/1996 | Robl | 540/521 |
| 5,552,397 A | | 9/1996 | Karanewsky et al. | 514/212 |
| 5,587,375 A | | 12/1996 | Robl | 514/213 |
| 5,635,504 A | | 6/1997 | Ryono et al. | 514/218 |
| 5,650,408 A | | 7/1997 | Karanewesky et al. | 514/214 |

FOREIGN PATENT DOCUMENTS

| EP | 743319 | 11/1996 |
|---|---|---|

OTHER PUBLICATIONS

Cleland, Dithiothreitol, a New Protective Reagent for SH Groups Biochem., 3(4), pp. 480–482, 1964.*
Suk–Wah Tam–Chang et al., Langmuir, 11, 1995, 4371–4382.
Warshawsky et al., Bioorganic & Med. Chem. Letters, vol. 6, No. 8, 304–305 (1994).
Robl et al., J. Med. Chem., 39, 1996, 494–502.
Skiles et al., J. Med. Chem. 29, 1986, 784–796.
Martin et al., J. Med. Chem., 28, 1985, 910–914.
Nardi et al., II Farmaco– Ed. Sc, vol. 40, 1985, pp. 108–119.
Podkoscielny et al., Przemysl Chemiczny, vol. 73, No. 8, 304–305 (1994).

* cited by examiner

*Primary Examiner*—Bruck Kifle
(74) *Attorney, Agent, or Firm*—Stephen B. Davis

(57) ABSTRACT

Acylmercaptoalkanoylamino lactam esters or acids are converted to the corresponding mercaptoalkanoylamino lactam ester or acid under basic conditions by including an agent which minimizes the amount of disulfides. Suitable agents are bismercaptans, phosphine or phosphite reducing agents, zinc metal powder, and sodium hydrosulfite. Such agents are also employed in the recrystallization and reprocessing of the mercaptoalkanoylamino lactam acids.

10 Claims, No Drawings

DEPROTECTION AND RECRYSTALLIZATION PROCESSES

This application claims priority from application Ser. No. 60/070,573 filed Jan. 6, 1998.

BACKGROUND OF THE INVENTION

Mercaptoalkanoylamino lactams have been disclosed as possessing useful cardiovascular properties as a result of their activity as dual angiotensin converting enzyme inhibitors and neutral metalloendopeptidase inhibitors. The lactam can be a moncyclic, fused bicyclic or fused tricyclic as taught by Karanewsky et al. in U.S. Pat. No. 5,552,397, Karanewsky in U.S. Pat. No. 5,504,080, Robl in U.S. Pat. No. 5,508,272, Robl in U.S. Pat. No. 5,525,723, Robl in U.S. Pat. No. 5,362,727, Robl in U.S. Pat. No. 5,587,375, Robl et al. in U.S. Ser. No. 443,278 filed May 17, 1995 and EP 744,319, Ryono et al. in U.S. Pat. No. 5,635,504 and Karanewsky et al. in U.S. Pat. No. 5,650,408.

These references disclose coupling an acylmercaptoalkanoic acid sidechain to the amino lactam ester followed by deprotection by treatment with sodium hydroxide or lithium hydroxide in aqueous alcohol or tetrahydrofuran followed by treatment with aqueous acid to give the desired mercaptoalkanoylamino lactam products.

SUMMARY OF THE INVENTION

This invention is directed to an improvement in the deprotection processes used to convert an acylmercaptoalkanoylamino lactam acid or ester of the formula

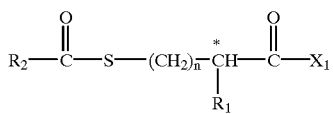
(II)

to the mercaptoalkanoylamino lactam acid or ester of the formula

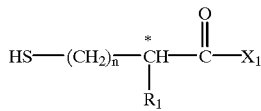
(I)

and an improvement in the deprotection process used to convert the mercaptoalkanoylamino lactam ester of formula I to the mercaptoalkanoylamino lactam acid of formula I.

These deprotection reactions are performed under basic conditions. The mercapto group in the lactam acid or ester of formula I under such conditions is susceptible to the formation of disulfides of the formula

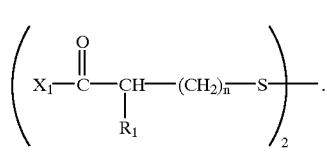
(III)

Such disulfides are themselves an unwanted impurity in the pharmaceutically active mercaptoalkanoylamino lactam acid products of formula I. Also, the disulfides of formula III can convert to other undesirable side-products. In particular, when $R_1$ is other than hydrogen, the disulfide of formula III can convert to the mercaptoalkanoyl lactam of formula I having the undesired chirality at the optically active carbon in the mercaptoalkanoyl sidechain.

Similarly, the formation of the disulfide impurity of formula III can occur during recrystallization of the mercaptoalkanoylamino lactam product of formula I.

The improvements of this invention reside in including within the above deprotection and recrystallization processes an agent that minimizes the amount of the disulfides of formula III and, in turn, minimizes the formation of the undesired epimer of the pharmaceutically active compound of formula I.

Preferred agents for this purpose are bismercaptans as well as reducing agents such as phosphines and phosphites, zinc metal powder, and sodium hydrosulfite.

DETAILED DESCRIPTION OF THE INVENTION

The amino lactam acids and esters $X_1$ shown above include:

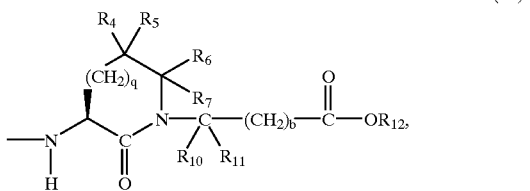
(IV)

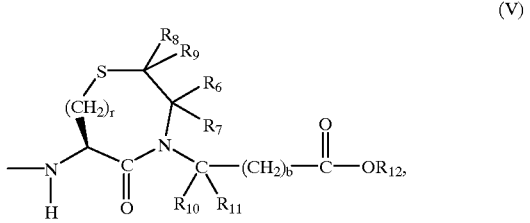
(V)

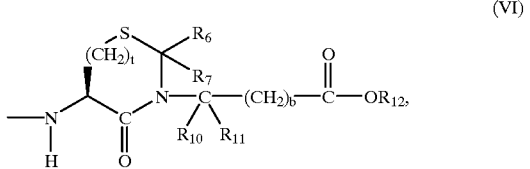
(VI)

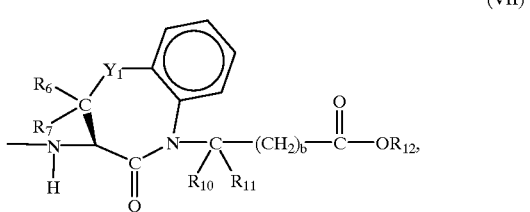
(VII)

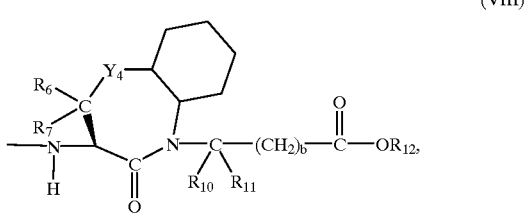
(VIII)

(IX)
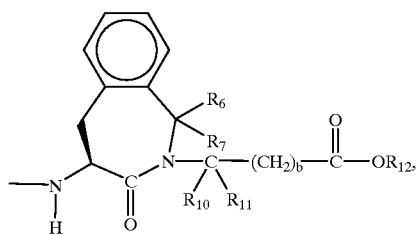
(X)
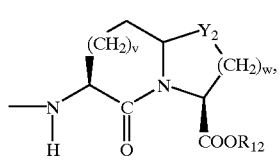
(XI)
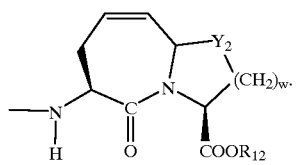
(XII)
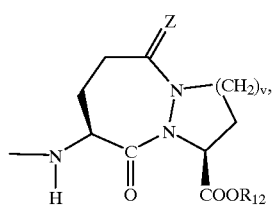
(XIII)
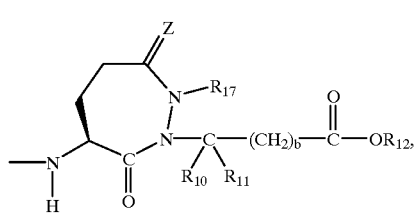
(XIV)
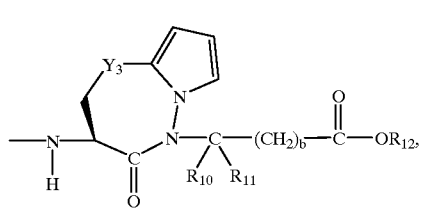
(XV)
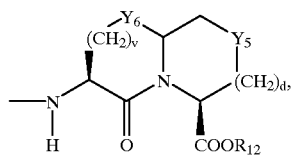
(XVI)
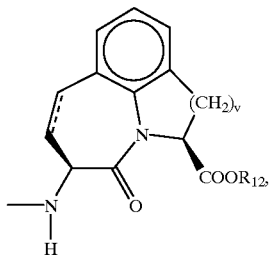
(XVII)
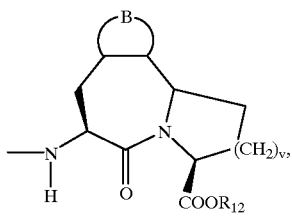
(XVIII)
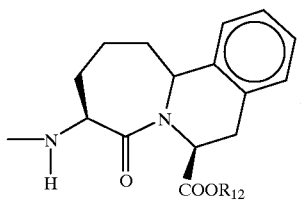
,
(XIX)
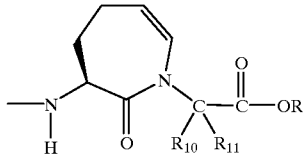
(XX)
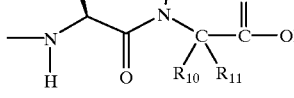
(XXI)
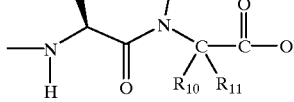
(XXII)
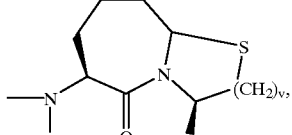 and -continued (XXIII)

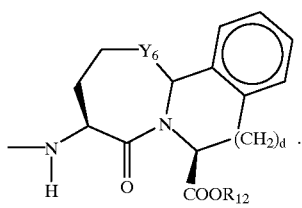

$Y_7$ is —S— or —NH—

$Y_8$ is —S—, —O— or —NH—

$R_{18}$ and $R_{19}$ are independently selected from hydrogen, alkyl, —$(CH_2)_m$-aryl, or $R_{18}$ and $R_{19}$ together with the carbon and nitrogen atoms to which they are attached complete a five or six membered ring.

$R_{12}$ is hydrogen or an acid protecting group such as methyl, ethyl, propyl, phenyl or benzyl.

The term "alkyl" refers to straight or branched radicals of 1 to 7 carbons, preferably 1 to 4 carbons.

The term "substituted alkyl" refers to such straight or branched chain radicals of 1 to 7 carbons wherein one, two or three hydrogens have been replaced by a hydroxy, amino, cyano, Cl, Br, F, trifluoromethyl, —NH(alkyl of 1 to 4 carbons), —N(alkyl of 1 to 4 carbons)$_2$, alkoxy of 1 to 4 carbons, alkylthio of 1 to 4 carbons, or carboxy. The preferred "substituted alkylf" is of 1 to 4 carbons with one hydrogen replaced by hydroxy, amino, Cl, or Br.

The term "alkenyl" refers to straight or branched chain radicals of 3 to 7 carbon atoms having one or two double bonds. Preferred "alkenyl" groups are straight chain radicals of 3 to 5 carbons having one double bond.

The term "cycloalkyl" refers to saturated rings of 3 to 7 carbons with cyclopropyl, cyclobutyl, cyclopentyl, and cyclohexyl being preferred.

The term "aryl" refers to phenyl, 1-naphthyl and 2-naphthyl with phenyl being preferred.

The term "substituted aryl" refers to phenyl, 1-naphthyl and 2-naphthyl having a substituent selected from alkyl of 1 to 4 carbons, alkoxy of 1 to 4 carbons, alkylthio of 1 to 4 carbons, Cl, Br, F, hydroxy,

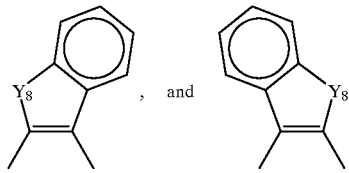

In the above formulas, the various symbols have the definitions listed below.

$R_1$ and $R_2$ are independently selected from straight or branched chain alkyl of 1 to 6 carbons, —$(CH_2)_m$-aryl, —$(CH_2)$m-substituted aryl, or —$(CH_2)_m$-heteroaryl.

m is zero or an integer from 1 to 6.

n is zero or one.

$R_4$ and $R_5$ are independently selected from hydrogen, alkyl, substituted alkyl, alkenyl, —$(CH_2)_m$-cycloalkyl, —$(CH_2)_m$-aryl, —$(CH_2)_m$-substituted aryl, or —$(CH_2)_m$-heteroaryl, or one of $R_4$ and $R_5$ is hydrogen and the other is hydroxy, or $R_4$ and $R_5$ taken together with the carbon to which they are attached complete a saturated cycloalkyl ring of 3 to 7 carbons, or $R_4$ and $R_5$ taken together with the carbon to which they are attached complete a keto substituent.

$R_6$, $R_8$ and $R_{10}$ are independently selected from hydrogen, alkyl, substituted alkyl, alkenyl, —$(CH_2)_m$-cycloalkyl, —$(CH_2)_m$-aryl, —$(CH_2)_m$-substituted aryl, or —$(CH_2)_m$-heteroaryl.

$R_7$, $R_9$ and $R_{11}$ are independently selected from hydrogen, alkyl, substituted alkyl, alkenyl, —$(CH_2)_m$-cycloalkyl, —$(CH_2)_m$-aryl, —$(CH_2)_m$-substituted aryl, or —$(CH_2)_m$-heteroaryl or $R_6$ and $R_7$ taken together with the carbon to which they are attached complete a saturated cycloalkyl ring of 3 to 7 carbons, or $R_8$ and $R_9$ taken together with the carbon to which they are attached complete a saturated cycloalkyl ring of 3 to 7 carbons.

b is zero or one.

d is zero or one.

q is an integer from 1 to 4.

r is one or two.

t is an integer from 1 to 3.

v is one or two.

w is one or two.

$Y_1$ is —$CH_2$—, —$(CH_2)_2$—, —$(CH_2)_3$—, —O—, —S—, —$CH_2$—O—, or —$CH_2$—S—.

$Y_2$ is —$CH_2$— —S—, or —O—.

$Y_3$ is —$CH_2$—, —$(CH_2)_2$, —$(CH_2)_3$—, —O— or —$CH_2$—O—.

Z is O or two hydrogens.

$R_{17}$ is hydrogen, alkyl, substituted alkyl, alkenyl, —$(CH_2)_m$-cycloalkyl, —$(CH_2)_m$-aryl, —$(CH_2)_m$-substituted aryl, or —$(CH_2)_m$-heteroaryl.

$Y_5$ is —$CH_2$—, —S—, or —O— provided that $Y_5$ is —S— or —O— only when d is one.

$Y_6$ is —S— or —O—.

the dashed line ---- represents an optional double bond between the two carbons.

represents an aromatic heteroatom containing ring selected from

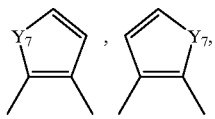

trifluoromethyl, amino, —NH(alkyl of 1 to 4 carbons), or —N(alkyl of 1 to 4 carbons)2, di and tri-substituted phenyl, 1-naphthyl, or 2-naphthyl wherein said substituents are selected from methyl, methoxy, Cl, Br, methylthio, hydroxy or amino.

The term "heteroaryl" refers to unsaturated rings of 5 or 6 atoms containing one or two O and S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl and 2- and 3-furyl. The term heteroaryl also includes bicyclic rings wherein the five or six membered ring containing O, S and N atoms as defined above is fused to a benzene or pyridyl ring. Preferred bicyclic rings are 2- and 3-indolyl and 4- and 5-quinolinyl.

The acylmercaptoamino lactam esters of formula II are prepared by coupling the acylmercapto containing sidechain of the formula

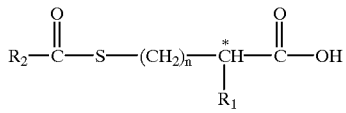
(XXIV)

with the amino lactam ester

 (XXV).

The above reaction can be performed in an organic solvent such as methylene chloride and in the presence of a coupling reagent such as 1-ethyl-3-(3-dimethylaminopropyl)carbodiimide, dicyclohexylcarbodiimide, benzotriazol-1-yloxytris-(dimethylamino)phosphonium hexafluorophosphate, or carbonyldiimidazole. Alternatively, the acylmercapto carboxylic acid of formula XXIV can be converted to an activated form such as an acid chloride, mixed anhydride, symmetrical anhydride, activated ester, etc., prior to coupling.

The starting materials of formulas XXIV and XXV and the resulting acylmercaptoalkanoylamino lactam esters of formula II are described in the prior art. For example, the above compounds wherein $X_1$ is as defined in formulas IV to XIV are described by Karanewsky et al. in U.S. Pat. No. 5,552,397 whose disclosure is hereby incorporated by reference. The above compounds wherein $X_1$ is as defined in formula XV are described by Robl in U.S. Pat. No. 5,508,272 whose disclosure is hereby incorporated by reference. The above compounds wherein $X_1$ is as defined in formula XVI are described by Karanewsky in U.S. Pat. No. 5,504,080 whose disclosure is hereby incorporated by reference. The above compounds wherein $X_1$ is as defined in formula XVII are described by Robl in U.S. Pat. No. 5,525,723 whose disclosure is hereby incorporated by reference. The above compounds wherein $X_1$ is as defined in formula XVIII are described by Robl in U.S. Pat. No. 5,362,727 whose disclosure is hereby incorporated by reference. The above compounds wherein $X_1$ is as defined in formula XIX and XX are described by Robl in U.S. Pat. No. 5,587,375 whose disclosure is hereby incorporated by reference. The above compounds wherein $X_1$ is as defined in formula XXI are described by Ryono et al. in U.S. Pat. No. 5,635,504 whose disclosure is hereby incorporated by reference. The above compounds wherein $X_1$ is as defined in formula XXII are described by Karanewsky et al. in U.S. Pat. No. 5,650,408 whose disclosure is hereby incorporated by reference. The above compounds wherein $X_1$ is as defined in formula XXIII are described by Robl et al. in EP 743,319 and in U.S. Ser. No. 443,278 filed May 17, 1995 whose disclosure is hereby incorporated by reference.

The deprotection processes of this invention include conversion of the acylmercaptoalkanoylamino lactam acid or ester of formula II to the mercaptoalkanoylamino lactam of formula I The improvement in this process resides in including in the basic hydrolysis reaction that removes the acyl functional group $R_2$—C(O)— an agent that minimizes the amount of the disulfides of formula III and, in turn, minimizes the formation of the undesired epimer of the pharmaceutically active compound of formula I.

When the acylmercaptoalkanoylamino lactam of formula II is a carboxylic acid, i.e. $R_{12}$ in the definition of $X_1$ in formula II is hydrogen, then the acyl protecting group $R_2$—C(O)— is removed in a single step to give the pharmaceutically active lactam of formula I. This deprotection process involves treating the lactam carboxylic acid of formula II with an alkali metal or alkaline earth metal hydroxide or carbonate or with an amine in a suitable solvent containing a sufficient amount of an agent that minimizes the amount of the disulfides of formula III. Suitable agents for this purpose include bismercaptans as well as phosphine and phosphite reducing agents, zinc metal powder, and sodium hydrosulfite. Such agents can be present in an amount from about 1 mole to about 20 mole percent, preferably from about 5 mole percent to about 10 mole percent in the reaction mixture. This deprotection reaction can be performed at a temperature of from about −20° C. to about 45° C. Following completion, the reaction is acidified with an aqueous acid such as HCl acetic acid, propanoic acid, sulfuric acid, phosphoric acid, or oxalic acid to precipitate out the pharmaceutically active lactam of formula I.

Suitable alkali metal and alkaline earth metal hydroxides and carbonates for this deprotection process include sodium hydroxide, potassium hydroxide, lithium hydroxide, sodium carbonate, potassium carbonate, and lithium carbonate. Amines useful in this deprotection process include $H_2N$-alkyl, $H_2N$—$(CH_2)_m$-aryl, and hydroxyalkylamines wherein alkyl, aryl, and m are as defined above. Methylamine, ethylamine, benzylamine, and ethanolamine are preferred. Suitable solvents for this deprotection process include methanol, aqueous methanol, ethanol, aqueous ethanol, tetrahydrofuran, aqueous tetrahydrofuran, isopropanol, aqueous isopropanol, acetonitrile, aqueous acetonitrile and water.

When the acylmercaptoalkanoylamino lactam of formula II is a carboxylic acid ester, i.e. $R_{12}$ in the definition of $X_1$ in formula II is an acid protecting group such as methyl, ethyl, propyl, phenyl or benzyl, then the acyl protecting group $R_2$—C(O)— and the carboxylic acid protecting group can be removed in a single step or in two steps to give the pharmaceutically active lactam of formula I. In the single step deprotection process, the lactam carboxylic acid ester of formula II is treated under aqueous conditions with an alkali metal or alkaline earth metal hydroxide or carbonate in a suitable solvent containing a sufficient amount of an agent that minimizes the amount of the disulfides of formula III. Suitable agents for this purpose include bismercaptans as well as phosphine and phosphite reducing agents, zinc metal powder, and sodium hydrosulfite. Such agents can be present in an amount from about 1 mole percent to about 20 mole percent, preferably from about 5 mole percent to about 10 mole percent in the reaction mixture. This deprotection reaction can be performed at a temperature of from about −20° to about 45° C. Following completion, the reaction is acidified with an aqueous acid such as HCl, acetic acid, propanoic acid, sulfuric acid, phosphoric acid, or oxalic acid to precipitate out the pharmaceutically active lactam of formula I.

Suitable alkali metal and alkaline earth metal hydroxides and carbonates for this one step deprotection process are as defined above. Suitable solvents for this one step deprotection process include methanol, ethanol, isopropanol, acetonitrile, and tetrahydrofuran. This reaction is performed under aqueous conditions meaning that water is present in the solvent and/or in the reagents.

The improved deprotection processes of this invention also include the process in which the acylmercaptoalkanoylamino lactam ester of formula II is converted to the mercaptoalkanoylamino lactam ester of formula I. This process involves removal of the acyl group $R_2$—C(O)— by treating the acylmercaptoalkanoylamino lactam ester of formula II with an alkali metal or alkaline earth hydroxide or carbonate or with an amine in a suitable solvent containing a sufficient amount of an agent that minimizes the amount of the disulfides of formula III and, in turn, minimizes the formation of the undesired epimer of the pharmaceutically active compound of formula I. Suitable agents for this purpose include bismercaptans as well as phosphine and phosphite reducing agents, zinc metal powder, and sodium hydrosulfite. Such agents can be present in an amount from about 1 mole percent to about 20 mole percent, preferably from about 5 mole percent to about 10 mole percent in the reaction mixture. When an alkali metal or alkaline earth metal hydroxide or carbonate is employed, the reaction is performed under non-aqueous conditions. When an amine is employed, the reaction is performed under aqueous conditions. This deprotection reaction is performed at a temperature of from about −20° C. to about 45° C. Following completion, the reaction is acidified with an aqueous acid such as HCl, acetic acid, propanoic acid, sulfuric acid, phosphoric acid or oxalic acid to precipitate out the mercaptoalkanoylamino lactam ester of formula I.

Suitable alkali metal and alkaline earth metal hydroxides and carbonates and amines for this first deprotection step are as defined above. Suitable solvents include methanol, ethanol, isopropanol, acetonitrile, and tetrahydrofuran.

The improved deprotection processes of this invention also include the process in which the mercaptoalkanoylamino lactam ester of formula I is converted to the pharmaceutically active mercaptoalkanoylamino lactam of formula I wherein $R_{12}$ is hydrogen. This process involves removal of the carboxylic acid protecting group by treating the lactam ester of formula I with an alkali metal or alkaline earth metal hydroxide or carbonate under aqueous conditions in a suitable solvent containing a sufficient amount of an agent that minimizes the amount of the disulfide of formula III, and in turn, minimizes the formation of the undesired epimer of the pharmaceutically active compound of formula I. Suitable agents for this purpose include bismercaptans as well as phosphine and phosphite reducing agents, and zinc metal powder. Such agents can be present at from about 1 mole percent to about 20 mole percent, preferably from about 5 mole percent to about 10 mole percent in the reaction mixture. This deprotection is performed at a temperature of from about −20° C. to about 45° C. Following completion, the reaction is acidified with an aqueous acid such as HCl, acetic acid, propanoic acid, sulfuric acid, phosphoric acid, or oxalic acid to precipitate out the pharmaceutically active lactam of formula I.

Suitable alkali metal and alkaline earth metal hydroxides and carbonates for this deprotection step are as defined above. Suitable solvents include water, methanol, ethanol, isopropanol, acetonitrile and tetrahydrofuran.

In the improved recrystallization and reprocessing process of this invention, the mercaptoalkanoylamino lactam product of formula I is added to a suitable solvent containing a sufficient amount of an agent that minimizes the amount of the disulfides of formula III, and in turn, minimizes the formation of the undesired epimer of the pharmaceutically active compound of formula I. Suitable agents for this purpose include bismercaptans as well as phosphine and phosphite reducing agents, zinc metal powder, and sodium hydrosulfite. Such agents can be present at from about 1 mole percent to about 20 mole percent, preferably from about 5 mole percent to about 10 mole percent in the recrystallization mixture. The resulting slurry is subjected to changes in temperature and/or pH, optionally filtered, and then subjected to additional changes in temperature and/or pH to effect the recrystallization. For example, the slurry can be heated at from about 25° C. to the reflux temperature to dissolve the solids, the solution is then filtered, the combined filtrates are cooled to about room temperature, and desired product is collected. Alternatively, the slurry is treated to raise the pH above at least about 8 by the addition of a basic material such as an alkali metal or alkaline earth metal hydroxide or carbonate, afterward the pH is lowered to at least below about 8 and preferably below about 6.0 and the product is precipitated out by the addition of an acid such as HCl, acetic acid, propanoic acid, sulfuric acid, phosphoric acid, or oxalic acid, the product is filtered off, washed with water and tert-butyl methyl ether, and dried in vacuo.

Suitable solvents for the recrystallization process include methanol, ethanol, isopropanol and mixtures thereof.

The bismercaptans employed in the above deprotection and recrystallization procedure are compounds which in the presence of the disulfide of formula III will cleave such disulfides by forming a stable ring. Suitable bismercaptans are those of the formula

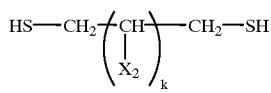

(XXVI)

wherein k is an integer from 1 to 4 and each $X_2$ is independently selected from hydrogen and hydroxy as well as 1,2-benzenedimethanethiol, 1,3-butanedithiol meso-α,α'-dimercaptoadipic acid, disodium salt, and durene-α(1), α(2)-dithiol. Preferred bismercaptans are dithiothreitol and dithioerythritol. Suitable phosphine reducing agents include tributyl phosphine and triphenyl phosphine. Suitable phosphite reducing agents include triethyl phosphite. The preferred reagent for use in the deprotection and recrystallization reactions of this invention is dithiothreitol.

By minimizing the amount of the disulfides of formula III in the reaction mixture according to the improved deprotection and recrystallization processes of this invention, the by-products of the disulfide of formula III are also minimized. Such by-products include, when $R_1$ is other than hydrogen, the mercaptoalkanylamino lactams of formula I having the undesired chirality at the optically active carbon in the sidechain.

In the preferred embodiments of this invention, $X_1$ in the acylmercaptoalkanoylamino lactam acid or ester of formula II is of formula IV or formula XV, n is zero, $R_1$ is benzyl, and $R_2$ is methyl. When $X_1$ is of formula IV, q is preferably two, $R_4$, $R_5$, $R_{10}$, and $R_{11}$ are preferably hydrogen, b is preferably zero, $R_{12}$ is preferably hydrogen or ethyl, and $R_6$ and $R_7$ are preferably independently selected from hydrogen and alkyl of 1 to 4 carbons, especially where $R_6$ and $R_7$ are both methyl. When $X_1$ is of formula XV, v is preferably two, d is preferably one, $Y_5$ is preferably —$CH_2$—, $Y_6$ is preferably —S—, and $R_{12}$ is preferably hydrogen or methyl.

The asterick (*) in formulas I, II and XXIV represent an asymmetric carbon in the acylmercaptoalkanoyl and mercaptoalkanoyl sidechain. In the preferred compounds, this asymmetric center has the absolute configuration S. As shown in formula IV to XXXIII other asymmetric centers are present in the various amino lactam rings.

The pharmaceutically active products of formula I wherein $R_{12}$ is hydrogen are useful cardiovascular agents particularly useful in the treatment of hypertension and congestive heart failure. The pharmaceutically active products can be formulated in amounts effective for treating hypertension or congestive heart failure as described by Karanewsky et al. in U.S. Pat. No. 5,552,397, Karanewsky in U.S. Pat. Nos 5,504,080 and 5,650,408, Robl in U.S. Pat. Nos. 5,508,272, 5,525,723, 5,587,375 and 5,362,727, Robl in U.S. Ser. No. 443,278 filed May 17, 1995 and EP 743,319 and, Ryono et al. in U.S. Pat. No. 5,635,504.

The following examples are illustrative of the invention.

EXAMPLE 1

[4S-[4α(R*), 7α, 10aβ]]-Octahydro-4-[(2-mercarto-1-oxo-3-phenylpropyl)amino]-5-oxo-7H-pyrido [2,1-b][1,3]thiazepine-7-carboxylic acid

[4S-[4α(R*), 7α, 10aβ]]-Octahydro-4-[[2-(acetylthio)-1-oxo-3-phenylpropyl]amino]-5-oxo-7H-pyrido[2,1-b][1,3]thiazepine-7-carboxylic acid, methyl ester (5.0 g, 10.76 mmole) [prepared as described in any of Examples 3(c), 11(i), 22(b), 23(i), or 24 of U.S. Pat. No. 5,508,272] was dissolved in methanol (45 ml) in a 250 ml flask equipped with an addition funnel, internal temperature probe and argon inlet. To the solution was added DL-dithiothreitol (83 mg, 0.538 mmole). The solution was sparged with argon for 15 minutes and then kept under argon. The solution was cooled to 0° C. in an ice bath. In the addition funnel, 1N sodium hydroxide solution (65 ml, 64.57 mmole) was sparged with argon for 30 minutes. The sparged sodium hydroxide solution was added to the reaction flask over 20 minutes so that the internal temperature did not exceed 5° C. The reaction was allowed to stir at 0° C. for 30 minutes, and then the ice bath was removed to allow the reaction to warm to room temperature over one hour. The reaction was stirred at room temperature for an additional two hours at which point TLC confirmed that the reaction was complete. A pH probe and a reflux condenser were attached to the reaction flask. The reaction was acidified with previously argon-sparged 3N HCl solution to a pH between 8 and 9. The mixture was warmed to 40° C. (internal temperature probe) and further acidified with vigorous stirring to pH 2. The resulting slurry was stirred at 40° C. for 30 minutes and then allowed to cool to room temperature for one hour. The product was collected by filtration and washed with distilled water (80 ml volumes) until the wash-water tested negative for chloride with silver nitrate solution. The product was washed with additional water (2×25 ml) and air-dried for 30 minutes. The product was washed with t-butyl methyl ether (2×10 ml) and hexane (2×10 ml), air-dried, and dried under high vacuum overnight to give 4.00 g title product (94% yield) as a white crystalline solid; m.p. 205–207° (decomp.); $[\alpha]_D$=−68.0° (c=1, dimethylformamide). TLC: $R_f$=0.63 (silica gel, 2% acetic acid/ethyl acetate; visualized by UV light and ceric sulphate/ammonium molybdate).

Anal. calc'd for $C_{19}H_{24}N_2O_4S_2$. 1.1 $H_2O$: C, 55.25; H, 5.98; N, 6.78; S, 15.52. Found: C, 55.10; H, 5.87; N, 6.74; S, 15.33.

EXAMPLE 2

[S-(R*,R*)]-Hexahydro-6-[(2-mercarto-1-oxo-3-phenylpropyl) amino]-2,2-dimethyl-7-oxo-1H-azepine-1-acetic acid

[S-(R*,R*)]-Hexahydro-6-[[2-(acetylthio)-1-oxo-3-phenylpropyl]amino]-2,2-dimethyl-7-oxo-1H-azepine-1-acetic acid, ethyl ester (2.0 g, 4.46 mmole) [prepared as described in Example 66 (g) of U.S. Pat. No. 5,552,397] was dissolved in methanol (9 ml) in a 100-ml flask equipped with an addition funnel, internal temperature probe and argon inlet. To the solution was added DL-dithiothreitol (34 mg, 0.22 mmole). The solution was sparged with argon for 15 minutes and then kept under argon. The resulting solution was cooled to 0° C. in an ice-bath. In the addition funnel, 1N sodium hydroxide (26.8 ml, 26.8 mmole) was sparged with argon for 30 minutes. The sparged sodium hydroxide solution was added to the reaction flask over 30 minutes so that the internal temperature did not exceed 5° C. The reaction was allowed to stir at 0° C. for 30 minutes and then the ice-bath was removed to allow the reaction to warm to room temperature over one hour. The reaction was stirred at room temperature for an additional 1.5 hours at which time TLC showed that the reaction was complete. A pH probe was attached to the reaction flask. The reaction was acidified with previously sparged 3N HCl to a pH of 6. As few seed crystals were added and the mixture was stirred for 5 minutes. The mixture was then further acidified to pH 2. The resulting slurry was stirred at room temperature for one hour. The product was collected by filtration and washed with distilled water until the wash-water tested negative for chloride with silver nitrate solution. The product was air-dried for 30 minutes, washed with t-butyl methyl ether (2×4 ml) and hexane (2×4 ml), air-dried, and dried under a high vacuum to give 1.5 g of title product as a white crystalline solid (89% yield), m.p. 176°–177°; $[\alpha]_D$=−18.1° (c=1.0, chloroform) TLC:$R_f$=0.51 (silica gel, 2% acetic acid/ethyl acette; visualized by UV light and ceric sulphate/ammonium molybdate).

Anal. calc'd for $C_{19}H_{26}N_2O_4S$.2.6 $H_2O$: C, 60.30; H, 6.92; N, 7.40; S, 8.47. Found: C, 60.02; H, 6.81; N, 7.34; S, 8.60.

EXAMPLE 3

[4S-[4α(R*), 7α, 10aβ]]-Octahydro-4-[(2-mercapto-1-oxo-3-phenylpropyl)amino]-5-oxo-7H-pyrido[2,1-b[]1,3]thiazeine-7-carboxylic acid, methyl ester

[4S-[4α(R*), 7α, 10aβ]]-Octahydro-4-[[2-(acetylthio)-1-oxo-3-phenylpropyl]amino]-5-oxo-7H-pyrido[2, 1-b][1, 3]thiazepine-7-carboxylic acid, methyl ester (700 g, 1.51 moles) was dissolved in methanol (7.71) in a 10 l flask equipped with an internal temperature probe and argon inlet. To the solution was added D,L-dithiothreitol (24.6 g, 0.16 moles). The solution was thoroughly purged with argon for 30 minutes. The solution as cooled to −15° C. and finely ground potassium carbonate (311.6 g, 2.25 moles) was added with agitation. After completion of the reaction (no starting material was detected by either TLC or HPLC), the potassium carbonate was removed by filtration. The filter cake was washed with methanol (400 ml). The temperature of the filtrate was kept at 0° C. while it was transferred to another 10 l flask.

Concentrated HCl (280 ml) which had been purged with argon was added rapidly with agitation. The desired product crystallized immediately and the resulting suspension was agitated at 10° C. for 30 minutes. Ice water (3.5 l) was added and the suspension was agitated at 0° C. for one hour. The crystals were collected by filtration. The product was washed with 1.8 l of methanol/water (2:1) at 0° C. followed by 1 l of cold water and finally washed twice with 1 l portions of methyl-tert-butyl ether and dried to give 594 g (93.5%) of title compound as a solid.

EXAMPLE 4

[4S-[4α(R*), 7α, 10aβ]]-Octahydro-4-[(2-mercapto-1-oxo-3-phenylpropyl)amino]-5-oxo-7H-pyrido[2,1-b][1,3]thiazeiine-7-carboxylic acid, methyl ester A slurry of [4S-[4α(R*), 7α, 10aβ]]-4-aminooctahydro-5-oxo-7H-pyrido[2,1-b][1,3]thiaze-pine-7-carboxylic acid, methyl ester, hydroiodide (150 g, 0.388 mol) and α-(acetylthio)benzenepropanoic acid, dicyclohexylamine salt (181.2 g, 0.447 mol) in methylene chloride (525 ml) was cooled to about −20° C. and treated with a slurry of N-ethyl-N'-dimethylaminopropylcarbodiimide (100.5 g, 0.524 mol) in methylene chloride (500 ml) while maintaining the pot temperature at less than −5° C. Additional methylene chloride (175 ml) was used to complete the transfer of the carbodiimide. The reaction was stirred at −5° to −12° C. until complete as determined by HPLC (about 18 hours). The cold reaction was filtered into dilute phosphoric acid (450 ml, 1:3 v/v of 85% phosphoric acid to water) and the filter cake was washed with methylene chloride (3×100 ml). The phases of the filtrate were separated and methyl tert-butyl ether (1000 ml) was added to the organic layer. The solvents were removed under vacuum to a pot volume of about 900 ml, and the slurry was filtered. The filter cake was washed with methyl tert-butyl ether (3×55 ml) and the filtrate was diluted with additional methyl tert-butyl ether (750 ml). The organic phase was washed with dilute phosphoric acid (450 ml, 1:3 v/v of 85% phosphoric acid to water), aqueous sodium bisulfite (3% w/v, 450 ml), and 5% aqueous sodium chloride (450 ml). The organic solution was filtered to remove any insoluble material and treated with D,L-dithiothreitol (6 g). Degassed methanol (2000 ml) was added and the solvents were distilled at about 20 mm of mercury until the pot volume was about 2200 ml. The solution of [4S-[4α(R*), 7α, 10aβ]]-octahydro-4-[[2-(acetylthio)-1-oxo-3-phenylpropyl]amino]-5-oxo-7H-pyrido[2,1-b][1,3]thiazepine-7-carboxylic acid, methyl ester was cooled to 0° to 5° and treated with 40% aqueous methylamine (150 ml) while maintaining the pot temperature at less than 5° C. The reaction was stirred for about 30 minutes and the pH was adjusted to 7.5–8.3 using concentrated HCl (155 ml) containing D,L-dithiothreitol (2% w/v). The resulting slurry was stirred for 30 minutes at 5° C., the pH was readjusted to 7.5–8.3, if necessary, and the product was filtered and washed with cold, degassed 3:1 methanol/water (3×300 ml). Drying in vacuo afforded 134.1 g of the title product.

The above procedure was also carried out with the following modifications. A sodium bicarbonate wash was utilized before the treatment with D,L-dithiothreitol, acetonitrile was employed in place of methanol after the treatment with D,L-dithiothreitol, and the pH was adjusted employing D,L-dithiothreitol in acetic acid rather than concentrated HCl.

EXAMPLE 5

[S-(R*, R*)]-Hexahydro-6-[(2-mercapto-1-oxo-3-phenylproryl) amino]-2,2-dimethyl-7-oxo-1H-azepine-1-acetic acid a) [S-(R*,R*)]-6-[[2-(Acetylthio-1-oxo-3-phenylpropyl] amino]hexahydro-2,2-dimethyl-7-oxo-1H-azepine-1-acetic acid, 1,1-dimethylethyl ester A solution of (S)-6-aminohexahydro-2,2-dimethyl-7-oxo-1H-azepine-1-acetic acid, 1,1-dimethylethyl ester (0.781 g, 2.8 mmole) in methylene chloride (11 ml) was cooled in an ice-bath and powdered (S)-2-(acetylthio)benzenepropanoic acid (0.641, 2.86 mmole) was added. A clear solution was obtained in a minute. 1-(3-Dimethylaminopropyl)-3-ethylcarbodiimide hydrochloride (0.642 g, 3.351 mole) was added and the mixture was stirred for 2.5 hours. The solvent was evaporated and the residue was taken up in ethyl acetate (25 ml) and 1N HCl (15 ml). The aqueous layer was separated and extracted with ethyl acetate (25 ml). The combined organic extracts were washed successively with 1N HCl (2×15 ml), brine, saturated aqueous sodium bicarbonate (2×10 ml) and brine (10 ml). The solution was dried over sodium sulfate and evaporated to give 1.32 g (93% yield) of title product as a white foam. $[\alpha]_D=-48.9°$ (c=1, ethyl acetate).

Anal. calc'd for $C_{25}H_{36}N_2O_5S \cdot 0.4H_2O$: C, 62.06; H, 7.67; N, 5.79, S, 6.63. Found: C, 62.28; H, 7.63; N, 5.75, S, 6.44.

b) [S-(R*, R*)]-6-[[2-(Acetylthio)-1-oxo-3-phenylpropyl] amino]hexahydro-2,2-dimethyl-7-oxo-1H-azeine-1-acetic acid Trifluoroacetic acid (9.0 ml, 126 mmole) was added to a solution of the product from part (a) (3.75 g, 7.88 mmole) in methylene chloride (30 ml). After 5 hours, dibasic sodium phosphate (8.4 g, 59.1 mmole) dissolved in water (50 ml) was added to the reaction mixture chilled in an ice bath. The pH of the mixture dropped to 1.4 and was adjusted to 2.9 with 10N sodium hydroxide. The layers were separated and the organic layer was washed with a solution of dibasic sodium phosphate (0.5 g) in water (25 ml) after adjusting its pH to 2.9 with concentrated HCl. The layers were back-washed with methylene chloride (5 ml). The combined organic layers were dried over sodium sulfate and evaporated. The residue was dissolved in methylene chloride (6 ml) and heptane (24 ml) was added slowly with stirring over 20 minutes. The resulting mass of crystals were stirred overnight, filtered, washed with methylene chloride/heptane (1:9), and heptane, and dried under vacuum to give 3.08 (93% yield) of title product as colorless crystals; m.p. 160–161° C.; $[\alpha]_D=-46.6°$ (c=0.7, chloroform).

Anal. calc'd for $C_{21}H_{28}N_2O_5S \cdot 0.023H_2O$: C, 59.47; H, 6.67; N, 6.59; S, 7.54. Found C, 59.29; H, 6.61; N, 6.55; S, 7.56.

c) [S-(R*,R*)]-Hexahydro-6-[(2-mercapto-1-oxo-3-phenylpropyl) amino]-2.2-dimethyl-7-oxo-1H-azepine-1-acetic acid In a 100 ml flask equipped with an addition funnel, internal temperature probe, and argon inlet, the title product from part (b) (2.0 g, 4.76 mmole) and D,L-dithiothreitol (0.037 g, 0.24 mmole) were stirred in methanol (6.4 ml). The suspension was sparged with argon for 10 minutes, cooled to 1° C., and then kept under argon. In the addition funnel, 1N sodium hydroxide (19 ml, 19 mmole) was sparged with argon for 15 minutes. The sparged sodium hydroxide solution was added to the reaction flask over 20 minutes so that the internal temperature did not exceed 5° C. The reaction was stirred at 1° C. for 30 minutes, and then the ice bath was removed to allow the reaction to warm to room temperature over 1 hour. A pH probe and a reflux condenser were attached to the reaction flask. The reaction was acidified with previously sparged 3N HCl solution to pH 6. The reaction was warmed to 40° C. (internal temperature probe). A few seed crystals of the desired product were added, and the mixture was further acidified with 3N HCl with stirring to pH 2. The resulting slurry was stirred at 40° C. for 30 minutes and then allowed to cool to room temperature over 1 hour.

The product was collected by filtration and washed with distilled water (about 30 ml) until the wash-water tested negative for chloride with silver nitrate solution. The product was air dried for 30 minutes, washed with tert-butyl methyl ether (2×4 ml) and hexane (2×4 ml), air-dried, and dried under high vacuum overnight to give 1.67 (93%) of title product as a white solid having the same analytical values as in Example 2.

EXAMPLE 6

[4S-[4α(R*), 7α, 10aβ]]-Octahydro-4-[(2-mercapto-1-oxo-3-phenylpropyl) amino]-5-oxo-7H-pyrido [2.1-b][1,3]thiazeine-7-carboxylic acid D,L-Dithiothreitol (10.4 g) was dissolved in methanol (3250 ml) and purged with inert gas to remove oxygen. The solution was cooled to 0–5° C. and the methyl ester product from Example 4 (296 g) was added. While stirring, 3N sodium hydroxide (1400 ml) was added at a rate so that the temperature was maintained at 0–5° C. After stirring for an additional 30 minutes, the reaction was warmed to room temperature. When the reaction was complete, the pH was adjusted to 1.6–2.0 by the addition of 3N HCl (1500 ml) resulting in crystallization of the product. During addition of the HCl the temperature rose to 30–35° C. Water (2800 ml) was then added, the slurry was cooled to room temperature over about one hour, and stirred for an additional hour. The product was filtered and washed with water (4×500 ml) and t-butyl methyl ether (4×500 ml). The product was then dried to give 272.4 g of title product having the same analytical values as in Example 1.

EXAMPLE 7

[4S-[4α(R*), 7α, 10aβ]]-Octahydro-4-[(2-mercapto-1-oxo-3-phenylpropyl)amino]-5-oxo-7H-pyrido[2,1-b][1,3]thiazeine-7-carboxylic acid All operations were performed under an argon atmosphere and all transfers were performed using cannulas to minimize exposure of the substrate and product to atomospheric oxygen.

Degassed 1N hydroxide (376 g, dissolved oxygen level is less than or equal to 5%) was added to a 1 liter four necked flask equipped with a mechanical stirrer, pH electrode, thermocouple, and argon inlet, containing the methyl ester product from Example 4 (50 g) and D,L-dithiothritol (1.8 g). The reaction solution was stirred at 20°±10° C. until hydrolysis was judged complete (HPLC assay, hydrolysis was complete about one hour after the addition of the sodium hydroxide was completed). The product solution was polish filtered to remove any particles, and the hydrolysis vessel and polish filter were washed with water (50 g). The filtrates were combined in a 1 liter four necked flask equipped with a mechanical stirrer, pH electrode, thermocouple and argon inlet. With vigorous agitation, the title compound was crystallized at 20°±10° C. by the addition of degassed lN acetic acid (401 g, dissolved oxygen level is less than or equal to 5%) to a final pH of 5.5±0.5. The crystal slurry was agitated at 20±10° C. for at least one hour, collected on a filter (inert atmosphere was no longer employed), and the wet-cake was washed with water (3×100 g). The wet-cake was dried in vacuo to afford 45.1 g of title product as a white crystalline powder having the same analytical values as in Example 1.

EXAMPLE 8

Recrystallization Of [4S-[4α(R*), 7α, 10aβ]]-Octahydro-4-[(2-mercapto-1-oxo-3-phenylpropyl) amino]-5-oxo-7H-pyrido[2,1-b][1,3]thiazepine-7-carboxylic acid All operations were performed under an argon atmosphere and all transfers were performed using cannulas to minimize exposure of the product to atmospheric oxygen.

Degassed alcohol solution (302 g of absolute ethanol and 87 g of methanol, containing less than or equal to 5% oxygen) was added to a 1 liter flask equipped with a mechanical stirrer, reflux condenser, thermocouple, and an argon inlet, containing [4S-[4α(R*), 7α, 10aβ]]-octahydro-4-[(2-mercapto-1-oxo-3-phenylpropyl)amino]-5-oxo-7H-pyrido[2,1-b][1,3]thiazepine-7-carboxylic acid (11 g) and D,L-dithiothreitol (1.1 g). The resulting slurry was heated at reflux (about 75° C.) for about 2 hours to dissolve the solids. After cooling the solution to about 60° C., it was polish filtered into a 1 liter four neck flask equipped with a mechanical stirrer, reflux condenser, thermocouple, and argon inlet. The dissolution vessel and polish filter were washed with methanol (5 g). With stirring, the combined filtrates were cooled to 20°±10° C., and held at that temperature for at least one hour. The product was collected on a filter (inert atmosphere no longer required) and the wet-cake was washed with methanol (3×15 g). The wet-cake was dried in vacuo to afford 8.74 g of title product as a white crystalline powder.

EXAMPLE 9

Reprocessing of [S-(R*,R*)]-Hexahydro-6-[(2-mercapto-1-oxo-3-phenylrrolyl)amino]-2.2-dimethyl-7-oxo-1H-azeoine-1-acetic acid

[S-(R*,R*)]-Hexahydro-6-[(2-mercapto-1-oxo-3-phenylpropyl) amino]-2,2-dimethyl-7-oxo-1H-azepine-1-acetic acid (5 g, 13.2 mmole, HPLC 99.6 area percent), and D,L-dithiothreitol (180 mg, 1.67 mmol) were charged to a three necked flask. The flask was flushed with nitrogen and immersed in an ice bath. Cold (20° C.) deoxygenated sodium hydroxide solution (1.22 N, 40 ml) were added slowly while maintaining the reaction temperature below 100° C. After complete addition, cooling was removed and the resulting solution was allowed to warm to room temperature. The solution was heated to about 45° C. and deoxygenated acetic acid solution (1.06N, 50 ml) was added while maintaining the temperature of the mixture at about 450° C. The crystal slurry was stirred at about 45° C. for 30 minutes and then allowed to cool to room temperature. After stirring at room temperature for 30 minutes, the product was filtered, washed with water (50 ml) and dried in a vacuum oven at 51° C./4.1 inch Hg to afford 4.65 g of title compound having a laboratory HPLC of 99.9 area percent.

EXAMPLE 10

[S-(R*,R*)]-Hexahydro-6-[(2-mercapto-1-oxo-3-phenylpropyl) amino]-2,2-dimethyl-7-oxo-1H-azepine-1-acetic acid A three necked flask was charged with [S-(R*,R*) ]-6-[[2-(acetylthio)-1-oxo-3-phenylpropyl]amino]hexahydro-2,2-dimethyl-7-oxo-1H-azepine-1-acetic acid (10 g, 23.78 mmoles) and D,L-dithiothreitol (390 mg, 2.5 mmoles). The flask was flushed with nitrogen. Deoxygenated water (20 ml) was added to the flask and the mixture was cooled to 1° C. Cold (1° C.) deoxygenated sodium hydroxide solution (1.22 N, total 70 ml, 84 mmoles) was added slowly while maintaining the temperature of the reaction mixture between 1° C. and 4° C. After addition of the initial 10 v/v% of the sodium hydroxide solution, the remainder of the solution was added, maintaining the reaction temperature between −2° to 30° C. After stirring the reaction mixture at −2° to 6° C. for 30 minutes, the reaction mixture was allowed to warm to room temperature. The reaction mixture was polish filtered into a crystallization flask and heated to 45° C. Deoxygenated acetic acid solution (1.06 N, 90 ml, 95 mmoles) was added while maintaining the reaction temperature between 41° and 46° C. The crystal slurry was stirred at 41° to 46° C. for 20 minutes and then allowed to cool to room temperature. After stirring at room temperature for 30 minutes, the product was filtered and washed with water (100 ml) and dried in a vacuum oven at 51° C./4.1 inch Hg to afford 8.45 g of title product having laboratory HPLC of 99.75 area percent.

EXAMPLE 11

[S-(R*,*)]-Hexahydro-6-[(2-mercato-1-oxo-3-phenylpropyl) amino]-2.2-dimethyl-7-oxo-1H-azepine-1-acetic acid a) [S-(R*,R*)]-Hexahydro-6-[(2-mercapto-1-oxo-3-phenylpropyl) amino]-2.2-dimethyl-7-oxo-1H-azepine-1-acetic acid, ethyl ester Under an inert atmosphere, a methylene chloride solution (25 ml) of (S)-2-(acetylthio)benzenepropanoic acid (4.8 g) was cooled to −11° C. and (chloromethylene) dimethyl-ammonium chloride (3.9 g) was added. The reaction mixture was stirred between −14 and −5° C. for 2 hours. To a separate reaction vessel, the camphorsulfonic acid salt of (S)-6-aminohexahydro-2,2-dimethyl-7-oxo-1H-azepinine-1-acetic acid, ethyl ester (10 g), potassium bicarbonate (12 g), methylene chloride (25 ml), and water (50 ml) were charged. After 10 minutes of stirring a biphasic solution was obtained and cooled to 0° C. With vigorous stirring, the methylene chloride solution of (S)-2-(acetylthio) benzenepropanoyl chloride was added to the biphasic reaction mixture maintaining the pH in the range of 6.8 to 8.5 and the temperature between 0 to 5° C. Once the reaction was judged complete by in-process HPLC assay, the phases were separated and the product rich organic phase was concentrated to an oily residue under reduced pressure. The oily residue was dissolved in isopropanol (50 ml), concentrated to a residue again and the resulting residue was dissolved in isopropanol (40 ml). The resulting solution was cooled to 0° C. and deoxygenated by sparging with nitrogen for at least 15 minutes. D,L-Dithiothreitol (220 mg) and ethanolamine (4 ml) were charged and the reaction mixture was stirred at 0° C. until it was judged complete by HPLC analysis. The pH of the reaction mixture (at 10° C.) was adjusted to 8.56 using a deoxygenated 1 N acetic acid solution (40 ml) to afford a crystal slurry. The pH of the crystal slurry was further adjusted to 7.36 using glacial acetic acid (6 drops). After cooling further, the crystal slurry was stirred at 0° C. for 30 minutes, filtered, and the wet cake was washed with cold (3° C.) aqueous isopropanol (1:1, 44 ml). Initially, the product was suction dried for 1.5 hour under a nitrogen atmosphere and finally dried in a vacuum oven at 41° C. to afford 7.51 g (87.6 M%) of the title compound.

b) [S-(R*,R*)]-Hexahydro-6-[(2-mercapto-1-oxo-3-phenylproyl) amino]-2.2-dimethyl-7-oxo-1H-azepine-1-acetic acid The product from part (a) (5 g), D,L-dithiothreitol (130 mg) and deoxygenated water (18 ml) were charged to a reaction vessel. Under an inert atmosphere, the mixture as stirred at ambient temperature and a solution of sodium ydroxide (17.5 ml, approximately 2.2 N) was charged while maintaining the temperature between 21 and 25° C. A clear solution was observed for 5 minutes after the sodium hydroxide had been added and the reaction mixture was stirred until the reaction was judged complete by HPLC assay. The solution was heated to 45° C. and deoxygenated acetic acid (43 ml, approximately 1 N) was added to adjust the pH of the product slurry to 5.9. The product slurry was stirred at 45° C. for 30 minutes, cooled to ambient temperature, filtered and washed with water (50 ml). The wet cake was dried in a vacuum oven at 61° C. to afford 4.2 g (90.3 M%) of the title compound.

EXAMPLE 12

Recrystallization Of [4S-[4α(R*), 7α, 10aβ]]-Octahydro-4-[(2-mercapto-1-oxo-3-phenylpronyl)amino]-5-oxo-7H-pyrido[2,1-b][1,3]thiazegine-7-carboxylic acid A flask containing [4S-[4α(R*), 7α, 10aβ]]-octahydro-4-[(2-mercapto-1-oxo-3-phenylpropyl)amino]-5-oxo-7H-pyrido[2,1-b][1,3]thiazepine-7-carboxylic acid (50.42 g, 123.42 mmol) and D,L-dithiothreitol (1.915 g, 12.41 mmole) was deoxygenated and treated with a deoxygenated solution of sodium hydroxide (0.5 N, 1.3 equiv.). The product dissolves in 3 to 5 minutes to give a solution with pH 8–8.5. The resulting colorless to pale pink solution was filtered under nitrogen into a crystallizer, and the dissolution flask and filter were rinsed with deoxygenated water. The product was crystallized by the addition of deoxygenated aqueous acetic acid (1.5 equivalents) which was prepared by dissolving glacial acetic acid (11.11 g, 10.59 ml, 186.8 mmol) in deionized water (175.7 ml) and was then deoxygenated by being bubbled with nitrogen. The acetic acid solution was added over 10–15 minutes and the pH fell from 8.1 to 7.2. After initial crystallization, additional deoxygenated 1N acetic acid was added over 10 to 15 minutes to complete the crystallization. The final pH of the slurry was 5.3. The product slurry was stirred for 1 hour at 15–25° C., filtered, and washed with water and tert-butyl methyl ether. The desired product was dried under vacuum at 35–45° C. for 16 hours to give 49.39 g of product (98% weight yield) having a purity of greater than 99%.

What is claimed is:

1. A deprotection process for converting the acylmercaptoalkanoylamino lactam acid or ester of the formula

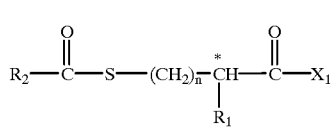

(II)

to the mercaptoalkanoylamino lactam acid or ester of the formula

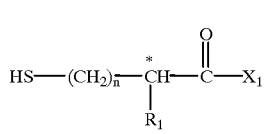

(I)

or for converting the mercaptoalkanoylamino lactam ester of formula I to the corresponding lactam acid of formula I wherein:

$X_1$ is a lactam of the formula

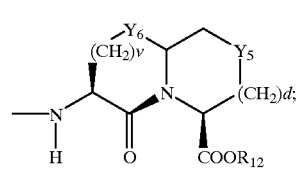

(XV)

$R_1$ and $R_2$ are independently selected from straight or branched chain alkyl of 1 to 6 carbons, —$(CH_2)_m$-aryl, —$(CH_2)_m$-substituted aryl, or —$(CH_2)_m$-heteroaryl;

m is zero or an integer from 1 to 6;
n is zero or one;
d is zero or one;
v is one or two;
$Y_5$ is —$CH_2$—, —S—, or —O— provided that $Y_5$ is —S— or —O— only when d is one;
$Y_6$ is —S— or —O—; and
$R_{12}$ is hydrogen or an acid protecting group selected from methyl, ethyl, propyl, phenyl or benzyl; which comprises;
a) when $R_{12}$ in the definition of $X_1$ in formula II is hydrogen, treating the acylmercaptoalkanoylamino lactam acid of formula II with an alkali metal or alkaline earth metal hydroxide or carbonate or with an amine in a suitable solvent containing a sufficient amount of an agent that minimizes the amount of the disulfides of the formula

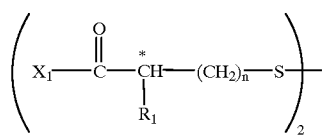

(III)

which, in turn, minimizes the formation of the undesired epimer of the pharmaceutically active compound of formula I followed by treatment with an aqueous acid to precipitate the desired lactam acid of formula I; or
b) when $R_{12}$ in the definition of $X_1$ in formula II is an acid protecting group, treating the acylmercaptoalkanoylamino lactam ester of formula II under aqueous conditions with an alkali metal or alkaline earth metal hydroxide or carbonate in a suitable solvent containing a sufficient amount of an agent that minimizes the amount of the disulfides of formula III which, in turn, minimizes the formation of the undesired epimer of the pharmaceutically active compound of formula I followed by treatment with an aqueous acid to precipitate the desired lactam acid of formula I; or
c) when $R_{12}$ in the definition of $X_1$ in formula II is an acid protecting group, treating the acylmercaptoalkanoylamino lactam ester of formula II under non-aqueous conditions with an alkali metal or alkaline earth metal hydroxide or carbonate in a suitable solvent containing a sufficient amount of an agent that minimizes the amount of the disulfides of formula III which, in turn, minimizes the formation of the undesired epimer of the pharmaceutically active compound of formula I or treating the acylmercaptoalkanoylamino lactam ester of formula II under aqueous conditions with an amine in a suitable solvent containing a sufficient amount of an agent that minimizes the amount of the disulfides of formula III which, in turn, minimizes the formation of the undesired epimer of the pharmaceutically active compound of formula I thus removing the acyl protecting group $R_2$—C(O)— to give the mercaptoalkanoylamino lactam ester of formula I; or
d) treating the mercaptoalkanoylamino lactam ester of formula I under aqueous conditions with an alkali metal or alkaline earth metal hydroxide or carbonate in a suitable solvent containing a sufficient amount of an agent that minimizes the amount of the disulfides of formula III which, in turn, minimizes the formation of the undesired epimer of the pharmaceutically active compound of formula I followed by treatment with an aqueous acid to precipitate the desired mercaptoalkanoylamino lactam acid of formula I.

2. The process of claim 1 wherein the agent that minimizes the amount of the disulfide of formula III is a bismercaptan of the formula

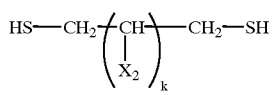

(XXVI)

wherein k is an integer from 1 to 4 and each $X_2$ is independently selected from hydrogen and hydroxy, or the bismercaptan is 1,2-benzenedimethanethiol, 1,3-butanedithiol meso-α, α'-dimercaptoadipic acid, disodium salt, or durene-α(1), α(2)-dithiol, or the agent is a phosphine or phosphite reducing agent, or the agent is zinc metal powder, or the agent is sodium hydrosulfite.

3. The process of claim 2 wherein the bismercaptan is dithiothreitol or dithioerythritol, the phosphine reducing agent is tributyl phospine or triphenyl phosphine, and the phosphite reducing agent is triethyl phosphite.

4. The process of claim 3 wherein:

$X_1$ is a lactam of the formula

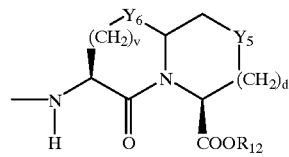

(XV)

$Y_6$ is S;

$Y_5$ is $CH_2$;

d is one;

v is two; and $R_{12}$ in the acylmercaptoalkanoylamino lactam of formula II is hydrogen or methyl and $R_{12}$ in the mercaptoalkanoylamino lactam of formula I is hydrogen.

5. The process of claim 4 wherein:

a) the acylmercaptoalkanoylamino lactam ester of formula II is [4S-[4α(R*), 7α, 10aβ]]-octahydro-4-[[2-(acetylthio)-1-oxo-3-phenyl-propyl]amino]-5-oxo-7H-pyrido[2,1-b][1,3]thiazepine-7-carboxylic acid, methyl ester which is dissolved in methanol and treated under aqueous conditions with D,L-dithiothreitol and sodium hydroxide; and b) following completion, the above reaction is treated with aqueous hydrochloric acid to precipitate [4S-[4α (R*), 7α, 10α]]-octahydro-4-[(2-mercapto-1-oxo-3-phenylpropyl)amino]-5-oxo-7H-pyrido[2,1-b][1,3]thiazepine-7-carboxylic acid.

6. The process of claim 3 wherein:

X₁ is a lactam of the formula

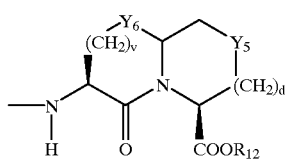

(XV)

$Y_6$ is S;

$Y_5$ is $CH_2$;

d is one;

v is two;

$R_{12}$ in the lactam esters of formula I and II is the same and is methyl, ethyl, propyl, phenyl or benzyl;

n is zero;

$R_1$ is benzyl; and the agent that minimizes the amount of the disulfide of formula III and, in turn, minimizes the formation of the undesired epimer of the pharmaceutically active compound of formula I is the bismercaptan dithiothreitol or dithioerythritol.

7. The process of claim 6 wherein:

the acylmercaptoalkanoylamino lactam ester of formula II is [4S-[4α(R*), 7α, 10aβ]]-octahydro-4-[[2-(acetylthio)-1-oxo-3-phenylpropyl]amino]-5-oxo-7H-pyrido[2,1-b][1,3]thiazepine-7-carboxylic acid, methyl ester which is dissolved in methanol and treated under non-aqueous conditions with D,L-dithiothreitol and potassium carbonate to give the mercaptoalkanoylamino lactam ester of formula I [4S-[4α(R*), 7α, 10aβ]]-octahydro-4-[(2-mercapto-1-oxo-3-phenylpropyl)amino]-5-oxo-7H-pyrido[2,1-b][1,3]thiazepine-7-carboxylic acid, methyl ester.

8. The process of claim 6 wherein:

the acylmercaptoalkanoylamino lactam ester of formula II is [4S-[4α(R*), 7α, 10aβ]]-octahydro-4-[[2-(acetylthio)-1-oxo-3-phenylpropyl]amino]-5-oxo-7H-pyrido[2,1-b][1,3]thiazepine-7-carboxylic acid, methyl ester which is dissolved in methanol or acetonitrile and treated under aqueous conditions with D,L-dithiothreitol and methylamine to give the mercaptoalkanoylamino lactam ester of formula I [4S-[4α(R*), 7α, 10aβ]]-octahydro-4-[(2-mercapto-1-oxo-3-phenylpropyl)amino]-5-oxo-7H-pyrido[2,1-b][1,3]thiazepine-7-carboxylic acid, methyl ester.

9. The process of claim 3 wherein:

X₁ is a lactam of the formula

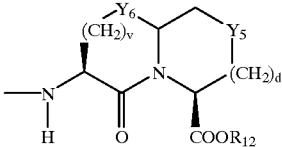

(XV)

$Y_6$ is S;

$Y_5$ is $CH_2$;

d is one;

v is two;

$R_{12}$ in the mercaptoalkanoylamino lactam ester of formula I is methyl, ethyl, propyl, phenyl or benzyl and $R_{12}$ in the mercaptoalkanoylamino lactam acid of formula I is hydrogen;

n is zero;

$R_1$ is benzyl; and the agent that minimizes the amount of the disulfide of formula III and, in turn, minimizes the formation of the undesired epimer of the pharmaceutically active compound of formula I is the bismercaptan dithiothreitol or dithioerythritol.

10. The process of claim 9 wherein a) the mercaptoalkanoylamino lactam ester of formula I is [4S-[4α(R*), 7α, 10aβ]]-octahydro-4-[(2-mercapto-1-oxo-3-phenylpropyl)amino]-5-oxo-7H-pyrido[2,1-b][1,3]thiazepine-7-carboxylic acid, methyl ester which is dissolved in methanol and treated under aqueous conditions with D,L-dithiothreitol and sodium hydroxide followed by aqueous acetic acid or hydrochloric acid to precipitate [4S-[4α(R*), 7α, 10aβ]]-octahydro-4-[(2-mercapto-1-oxo-3-phenylpropyl)amino]-5-oxo-7H-pyrido[2,1-b][1,3]thiazepine-7-carboxylic acid; or b) the mercaptoalkanoylamino lactam ester of formula I is [4S-[4α(R*), 7α, 10aβ]]-octahydro-4-[(2-mercapto-1-oxo-3-phenylpropyl)amino]-5-oxo-7H-pyrido [2,1-b][1,3]thiazepine-7-carboxylic acid, methyl ester which is slurried in water and treated with D,L-dithothreeitol and sodium hydroxide followed by aqueous acetic acid or hydrochloric acid to precipitate [4S-[4α(R*), 7α, 10aβ]]-octahydro-4-[(2-mercapto-1-oxo-3-phenylpropyl)amino]-5-oxo-7H-pyrido [2, 1-b][1, 3]thiazepine-7-carboxylic acid.

\* \* \* \* \*